US006458106B1

(12) United States Patent
Meier et al.

(10) Patent No.: US 6,458,106 B1
(45) Date of Patent: Oct. 1, 2002

(54) LOW PROFILE JEJUNAL ADAPTER FOR A GASTROJEJUNAL FEEDING SYSTEM

(75) Inventors: Kevin C. Meier, St. Louis, MO (US); Peter M. Von Dyck, Fernandina, FL (US); Scott Alan Ruddell, Waukegan; Glenn G. Fournie, Smithton, both of IL (US)

(73) Assignee: Sherwood Services, AG (CH)

( * ) Notice: Subject to any disclaimer, the term of this patent is extended or adjusted under 35 U.S.C. 154(b) by 0 days.

(21) Appl. No.: 09/505,520

(22) Filed: Feb. 17, 2000

(51) Int. Cl.[7] .......... A61M 5/00

(52) U.S. Cl. .......... 604/264; 604/175; 604/535; 604/910

(58) Field of Search .......... 604/910, 264, 604/174, 175, 533, 535, 537, 538, 539, 246, 247, 256

(56) References Cited

U.S. PATENT DOCUMENTS

| | | | |
|---|---|---|---|
| 4,668,225 A | 5/1987 | Russo et al. | |
| 4,685,901 A | 8/1987 | Parks | 604/96 |
| 4,701,163 A | 10/1987 | Parks | 604/178 |
| 4,798,592 A | 1/1989 | Parks | 604/49 |
| 5,248,302 A | 9/1993 | Patrick et al. | 604/178 |
| 5,342,321 A | 8/1994 | Potter | |
| 5,370,610 A | 12/1994 | Reynolds | |
| 5,399,173 A | 3/1995 | Park et al. | 604/282 |
| 5,527,280 A | 6/1996 | Goelz | |
| 5,851,195 A | 12/1998 | Gill | 604/49 |
| 5,902,285 A | 5/1999 | Kudsk et al. | 604/270 |

FOREIGN PATENT DOCUMENTS

| | | |
|---|---|---|
| DE | 19752430 A | 11/1997 |

*Primary Examiner*—Brian L. Casler
*Assistant Examiner*—Mark Han
(74) *Attorney, Agent, or Firm*—Greensfelder, Hemker & Gale, P.C.

(57) ABSTRACT

The present invention is a low profile jejunal adapter for a low profile gastrostomy tube. Once properly attached, the jejunal adapter converts the low profile gastrostomy tube into a gastrojejunostomy tube. Specifically, the jejunal adapter includes a feeding tube which is positioned within the jejunum of a patient and a venting lumen which provides for simultaneous venting of gases collected in the patient's stomach while fluid is being fed to the jejunum through the feeding tube. In a preferred embodiment, the length of the feeding tube is adjustable to accommodate various patients. In an alternative embodiment, the length of the feeding tube is fixed to reduce the manufacturing costs of this device. The jejunal adapter of this invention also includes a cap retention mechanism for securing the cap of the gastrostomy tube and a latch mechanism adapted to secure the jejunal adapter to the gastrostomy tube.

38 Claims, 5 Drawing Sheets

LOW PROFILE JEJUNAL ADAPTER FOR A GASTROJEJUNAL FEEDING SYSTEM

BACKGROUND OF THE INVENTION

1. Field of the Invention

The present invention relates to enteral feeding, and more particularly to a gastrojejunal feeding system. More specifically, the present invention relates to a jejunal adapter having a low profile configuration which permits venting of gas from the stomach while simultaneously providing fluid directly to the jejunum of a patient.

2. Prior Art

Enteral feeding is frequently used to assist patients who are ambulatory and/or in a combative state and require some sort of alternative feeding device to receive nutrition when unable to take nutrition orally. Typically, the patient is fed though a tube connected to a source of nutrition which is directed into a digestive organ of the patient through a feeding device. As used herein, the term feeding shall be interpreted to include nutritional feeding, medicating or hydrating.

Over the years a variety of feeding devices have been utilized. For instance, nasogastric or nasoenteric feeding devices have been used which direct a feeding tube into a patient's nose, through the nasal passage, down the esophagus and into either the stomach (nasogastric) or the small intestine (nasoenteric) of the patient. Both feeding devices operate satisfactorily to feed a patient by use of a relatively noninvasive procedure; however, each device also has several drawbacks. For instance, as the feeding tube is passed through the patient's nasal passage, it may become misdirected into the pulmonary tree which could result in discomfort or even harm to the patient, particularly if fluids are unintentionally administered through the feeding tube and into the pulmonary tree. Additionally, feeding tubes passed through the nasal passage may also result in local irritation, epistaxis, sinusitis, or various other complications to the patient.

In an attempt to advance the art of nasogastric and nasoenteric devices, lighter, smaller feeding tubes have been used to reduce irritation of the nasal passage. Although reducing discomfort, these type of feeding tubes were prone to kinking or clogging. Because of the above-noted deficiencies, nasal entry methods were typically used in short term applications for no longer than thirty days.

Since nasoenteric or nasogastric feeding devices were best suited for use in short term applications, a need existed for a device capable of long term deployment. A variety of surgical methods have been utilized such as a Stamms surgical gastrostomy in which the anterior gastric wall was lifted with a pair of guy sutures while the surgeon cut through the serosa and the muscular wall of the stomach to form a gastrostomy. A catheter was then introduced through the gastrostomy and into the stomach. Although a surgical gastrostomy was better suited for long-term applications, it was substantially more invasive to the patient and typically required use of a general anesthetic. Finally, as with any surgical procedure, the opportunity for infection or morbidity was increased.

In an attempt to provide a less invasive procedure for long-term access to the stomach, several percutaneous endoscopic gastrostomy methods have been suggested which access the stomach by a needle or cannula forced into the stomach. Generally, a percutaneous endoscopic gastrostomy (PEG) is performed in one of three methods: the pull technique, the push technique or the introducer technique.

In the pull technique, the gastrostomy tube was equipped with a wire loop through the proximal end of a catheter, while a cannula was slipped over the catheter so that a portion of the wire loop extended therefrom and a smooth transition from the wire loop to the cannula provided. A bolster or other similar stop member was attached at the distal end of the catheter and the gastrostomy tube was then deployed by an endoscopic procedure in which an endoscope was inserted down the patient's esophagus and into the stomach. Thereafter, the subcutaneous tissue was incised below the skin and a needle and cannula arrangement thrust through the incision adjacent the abdominal and gastric walls. Once the cannula penetrated the stomach wall, the needle was removed and the cannula was snared by a loop which extended from the endoscope. The physician then passed a length of suture through the cannula and into the patient's stomach. Once a sufficient length of the suture was directed into the patient's stomach, the snare was loosened from the cannula and retightened about the suture. The endoscope could then be removed which drew the snare and suture out through the patient's mouth. The gastrostomy tube was then tied to the suture extending from the patient's mouth and pulled back through the mouth, down the esophagus, into the stomach, and out through the gastrostomy until the bolster securely abutted the stomach wall. Finally, a retaining ring was fitted about the gastrostomy tube adjacent the patient's outer abdomen to secure the gastrostomy tube thereto.

Another method utilized to access the stomach was the push method. This method utilized an endoscope which was placed within the stomach through the patient's mouth. The skin and subcutaneous tissue could then be incised and a needle passed through the incision and pierced through the abdominal and stomach walls. Once the needle pierced through the stomach wall, a guide wire was passed through the needle and a snare deployed from the endoscope to capture the guide wire. As the endoscope was removed back through the mouth of the patient, the snare and guide wire were also pulled along and out the patient's mouth. As tension was maintained on the guide wire, a gastrostomy tube was pushed therealong until the proximal end of the gastrostomy tube extended outwardly from the gastrostomy. Once a portion of the gastrostomy tube extended from the gastrostomy, it was pulled the remainder of the distance outward until the bolster securely abutted the stomach wall. Finally, a retaining ring was fitted about the gastrostomy tube adjacent the patient's abdomen.

Another well known percutaneous endoscopic gastrostomy method was the introducer technique which involved thrusting a needle through the skin and into the stomach of a patient. Once the needle pierced through the stomach wall, a guide wire was threaded along the needle into the stomach and an incision was made about the guide wire. Next, the introducer set, which included an outer sheath and an inner dilator, was passed over the wire and into the stomach in order to dilate the incision. The physician then removed the inner dilator and wire leaving the outer sheath behind. A physician utilizing this method would then insert a catheter through the outer sheath and into the stomach. Thereafter, the outer sheath was frangibly peeled away and withdrawn from the patient leaving the catheter in place.

Although each of the above-described percutaneous endoscopic gastrostomy methods provided a relatively less invasive method than other surgical procedures, even these methods had drawbacks. Percutaneous endoscopic gastrostomy tubes extended a substantial distance outwardly from the patient might be deemed cosmetically undesirable by the patient. Moreover, even though these gastrostomy tubes could be deployed for a substantially greater period of time, they typically had to be removed and replaced after about six months.

In order to further advance the art, a variety of replacement gastrostomy tubes have been suggested. One such replacement gastrostomy tube is disclosed in U.S. Pat. No. 4,798,592 to Parks entitled "Gastrostomy Feeding Device" which describes a gastrostomy tube having an inflatable balloon and an adjustable ring. The gastrostomy tube was inserted through a matured stoma formed through the patient's stomach wall with the balloon in a deflated state. Once the distal end of the gastrostomy tube was properly positioned inside the patient's stomach, the balloon was inflated and the adjustable ring seated against the patient's outer abdomen so that the gastrostomy tube was secured in place.

Although the device disclosed by Parks provided a gastrostomy tube which could be inserted through a matured stoma of a patient, use of a gastrostomy tube with an inflated balloon proved too unreliable. An inflated balloon could become accidentally deflated which permitted inadvertent removal of the gastrostomy tube from the stoma. Patients were also known to experience discomfort when using such devices since the inflated balloon had an enlarged profile once expanded within the patient's stomach. Just as with the percutaneous endoscopic gastrostomy tubes, these gastrostomy tubes extended outwardly a substantial length from the patient which might be perceived as cosmetically unappealing. Moreover, it was found that in certain patients fluid contained within a patient's stomach could be unintentionally refluxed so that use of any of the above-mentioned gastrostomy tubes feeding directly into the stomach could present an unsafe or even life threatening situation.

Another advancement in the art to overcome some of the disadvantages of prior art gastrostomy tubes was the development of skin-level, or low profile, gastrostomy tube devices such as those disclosed in U.S. Pat. No. 5,248,302 to Patrick et al. entitled "percutaneous Obduratable Internal Anchoring Device" which is incorporated herein by reference. The Patrick et al. reference disclosed a gastrostomy tube comprising a tubular member having a deformable obduratable internal retention member at one end and an external retention member at the other end thereof for securing the tubular member inside the stomach. The internal retention member was designed to pass through a matured stoma of a patient and be elastically expanded outwardly in order to anchor the gastrostomy tube within the stomach. A plurality of flexible retaining arms with an orifice formed at the distal end thereof was provided at one end of a hollow tubular member, while an external retention member was provided at the other end of the tubular member. The external retention member included a body with an opening and a lumen formed therethrough with a pair of legs extending from the body adapted to abut the skin of the patient and prevent the tubular member from slipping completely through the matured stoma.

The above-described gastrostomy tube was deployed inside the patent's stomach by inserting an obturator rod through the lumen of the tubular member until the rod registered against the orifice formed between the flexible retaining legs of the internal retention member. By pushing the obturator rod axially against the retaining arms, the arms mechanically elongated and slenderized to a size slightly less than the inner diameter of the tubular member lumen. Slenderization of the retaining arms allowed safe insertion or removal of the internal retention member into, or from, an established, matured stoma of a patient through the tubular member. After the internal retention member was inserted inside the stomach, the obturator rod was then withdrawn through the lumen of the tubular member which caused the flexible retaining arms of the internal retention member to assume their preset enlarged shape, thereby anchoring the internal retention member against the stomach wall. Once the internal retention member was properly anchored, a tube administration set was connected to the opening of the external retention member to establish fluid flow communication between the source of fluid and a patient's stomach. In this way, fluid was provided to a patient through the gastrostomy tube.

Although such feeding devices provided a substantial improvement in the art by furnishing a low profile gastrostomy tube, even these devices could be further enhanced. Since gastrostomy tubes fed directly into the stomach of a patient, these devices were completely incapable of assisting patients prone to gastroesophageal reflux or aspiration caused by feeding fluid directly into the stomach. However, it was well known in the art that feeding fluid directly into the jejunal region of the small intestine of a patient, rather than into the stomach, drastically reduced the possibility for gastroesophageal reflux. Accordingly, several devices have been suggested which accessed the jejunum either directly by use of a jejunostomy or indirectly through a gastrojejunostomy wherein a feeding tube was inserted though a gastrostomy tube and passed through the pyloric sphincter and into the small intestine such that the distal end of the feeding tube terminated within the jejunum.

Another device typical of the art is described in U.S. Pat. No. 5,851,195 to Gill entitled "Direct Percutaneous Endoscopic Jejunostomy Method and Apparatus". The Gill device included a wire with a proximal end having a bend and a distal end having a piercing tip with a sheath which movably surrounds the piercing tip. The sheath and wire are deployed by use of an endoscope that passed the wire down the esophagus, through the pyloric sphincter and into the jejunum of the patient. The wire was then slid relative to the sheath so that it was emergent therefrom and driven through the abdominal walls. A percutaneous access tube was then attached to the proximal end of the wire. Once the percutaneous access tube was properly attached, the wire was pulled from its distal end in order to drag a portion of the access tube into the jejunum while a portion of the access tube extended a substantial length outwardly away from the patient for connection to a tube administration set.

Devices constructed in accordance with the teachings of Gill operated effectively to provide access to the jejunum while preventing gastroesophogeal reflux; yet, these devices had many of the same drawbacks found with the previous percutaneous endoscopic gastrostomy tubes. For instance, these devices had a tube which extended outwardly a substantial distance from the patient. Further, since devices in accordance with Gill had a single tube in communication solely with the jejunum, these devices were incapable of venting gases from the stomach while simultaneously feeding fluid directly to the jejunum.

Therefore, there appears to be a need in the art for a low profile jejunal feeding device. It would also be desirable to have a low profile jejunal feeding device which includes an adapter attachable to prior art low profile gastrostomy tubes. It would be further desirable to provide a low profile jejunal feeding device which allows for venting of air from the stomach while simultaneously providing fluid directly into the jejunum of a patient.

OBJECTS AND SUMMARY OF THE INVENTION

In brief summary, the present invention overcomes and substantially alleviates the deficiencies in the prior art by providing a low profile jejunal adapter for converting a low profile gastrostomy tube into a gastojejunostomy tube. The low profile jejunal adapter is configured to be used with a prior art low profile gastrostomy tube having a hollow tubular member with an external retention member attached at one end and an internal retention member attached at the other end for securing the tubular member within the stoma of a patient.

The external retention member comprises a body having a lumen formed therethrough and opposed legs which are adapted to abut the outer abdomen of a patient. Preferably, the internal retention mechanism comprises a plurality of flexible retaining arms with an orifice formed through the distal end thereof. The flexible retaining arms are releasably expandable within a patient's stomach using an obturator rod to insert and anchor internal retention member within a patient's stomach.

Alternatively, the internal retention member can have an inflatable balloon retention mechanism instead of flexible retaining arms which also anchors the low profile gastrostomy tube inside the patient's stomach. The balloon retention mechanism includes an inflatable balloon with a lumen which extends axially along the low profile gastrostomy tube and communicates with a one way valve. To inflate the balloon, the user engages a syringe or other suitable device and injects air through the one-way valve which inflates the balloon.

The low profile jejunal adapter of the present invention includes a body having opposing upper and lower surfaces and opposing forward and rearward portions. The body also includes a protrusion extending axially from the lower surface thereof with a primary lumen formed therethrough in communication with a channel also formed through the body. Further, the channel is longitudinally formed along the upper surface of the body having an arcuate shape which interconnects the primary lumen to the primary port. Extending from the primary port is a primary tubular extension which has a threaded cap attached to its free end. The protrusion is sized and shaped to be engageable within the opening of the external retention member such that the low profile jejunal adapter is securely engaged with the low profile gastrostomy tube.

The low profile jejunal adapter also includes a feeding tube for transporting fluid to the jejunum of the patient. The feeding tube is sized and shaped to be inserted through the pathway formed through the primary tubular extension, the channel and the primary lumen of the jejunal adapter as well as the low profile gastrostomy tube. The feeding tube includes a plurality of radial apertures formed proximate the distal end thereof to ensure proper fluid flow out of the feeding tube and into the jejunum. In addition, the feeding tube may also be adapted to include a plurality of weights located at the distal end thereof to assist in maintaining the distal end of the feeding tube within the jejunum or a coiled end to achieve the same result.

Once the distal end of the feeding tube is properly positioned within the jejunum, the proximal end of the feeding tube is threaded through the primary lumen along the channel and out the primary tubular extension such that the feeding tube extends approximately parallel relative to the abdomen of the patient, thereby presenting a substantially low profile relative to the patient. Once the distal end of the feeding tube is properly positioned within the jejunum of the patient, the proximal end of the feeding tube may then be cut to any desirable length and connected to a tube administration set using an adapter. The tube administration set is in turn connected to a fluid source.

Aside from the primary lumen, the low profile jejunal adapter further comprises a venting lumen formed axially through the protrusion having a generally banana-shaped configuration which permits the jejunal adapter to vent air from the stomach through the low profile gastrostomy tube and out the jejunal adapter, while simultaneously feeding fluid to the jejunum through the feeding tube. The venting lumen is in communication with a venting port formed at the rearward portion of the body. A venting tubular extension is connected to the venting port with a cap attached thereto for sealing the venting tubular extension during non-use.

Another unique aspect of the low profile jejunal adapter is that it includes a mechanism for latching and securing the jejunal adapter to a low profile gastrostomy tube inserted through a stoma of a patient. The latching mechanism includes a leg extending from the lower surface of the body with a finger formed at a distal end thereof. The leg functions to space the finger a distance from the body of the low profile jejunal adapter so that one of the legs of the external retention member may be securely nested between the lower surface and finger of the jejunal adapter.

The low profile of the jejunal adapter also includes a gastrostomy cap retention mechanism for retaining the tethered cap of the low profile gastrostomy tube. The gastrostomy cap retention mechanism comprises a depression formed in the upper surface of the body with a U-shaped groove formed in the forward portion of the upper surface, while a U-shaped undercut is located below and aligned with the U-shaped groove. The depression and U-shaped groove are sized and shaped to receive the cap, and shaft of the cap, respectively. Finally, the U-shaped undercut is adapted to receive the plug portion of the cap. Once properly nested therein, the cap is releasably retained by the cap retention mechanism.

An alternative embodiment of the low profile jejunal adapter is also contemplated and provides a jejunal adapter with enhanced cost effectiveness. The alternative embodiment of the low profile jejunal adapter comprises a body having an opposing upper and lower surfaces and opposing forward and rearward portions. The body comprises a protrusion axially extending from the lower surface with a primary lumen formed therethrough and a primary port formed through the body in communication with the primary lumen. The protrusion is sized and shaped to be receivable within the lumen of the external retention member of the low profile gastrostomy tube. A hole is formed through the upper surface which is aligned with the primary lumen for receipt of a stylet, or guide wire, to assist in directing a feeding tube into the jejunum. The body of the jejunal adapter also includes a pair of slots formed therethrough for returning a plate.

The plate is sized to be fitted over the upper surface of the body and has a pair of tabs adapted to be receivable within the pair of slots formed at the upper surface to secure the plate to the body once tabs are engaged within the slots. The plate further includes a plug member which is sized and shaped to seal the hole of the upper surface once the plate is secured to the body. The low profile jejunal adapter of the alternate embodiment also includes a feeding tube which is inserted through the primary lumen of the jejunal adapter for providing fluid to the jejunum.

Similar to the preferred embodiment, the alternative embodiment also includes a venting lumen formed through the protrusion of the body having a generally banana shaped cross-section which allows for venting of air from the stomach. The venting lumen is in communication with a venting port formed at the rearward portion of the body with a venting tubular extension which extends outwardly from the venting port and is oriented generally perpendicular relative to the venting lumen.

Another distinguishing feature of the alternative embodiment from the preferred embodiment is that the feeding tube is fixedly attached to the primary lumen of the low profile jejunal adapter. Since the distance to a patient's jejunum may vary from patient to patient depending on age or build, various low profile jejunal adapters are manufactured having feeding tubes with differing lengths to accommodate patients of different sizes.

Accordingly, the primary object of the present invention is to provide a jejunal feeding adapter which is adapted to be attachable to a low profile gastrostomy tube and is similarly configured to have a low profile orientation relative to a patient.

Another object of the present invention is to provide a low profile jejunal adapter which allows for venting of air from the stomach while simultaneously feeding fluid to the jejunum of a patient.

It is yet another object of the present invention to have a low profile jejunal adapter which can accommodate patients of various ages and differing builds.

These and other objects of the present invention are realized in the preferred embodiment of the present invention, described by way of example and not by way of limitation, which provides for a low profile jejunal feeding adapter having a low profile configuration which is attached to a low profile gastrostomy tube.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
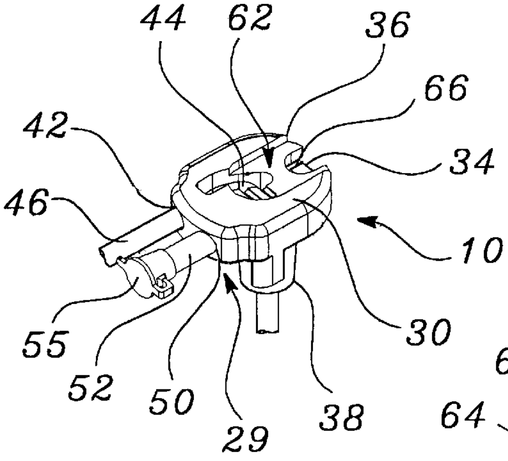
FIG. 1 is a perspective view of a preferred embodiment of a low profile jejunal adapter according to the present invention.
Figure 8:
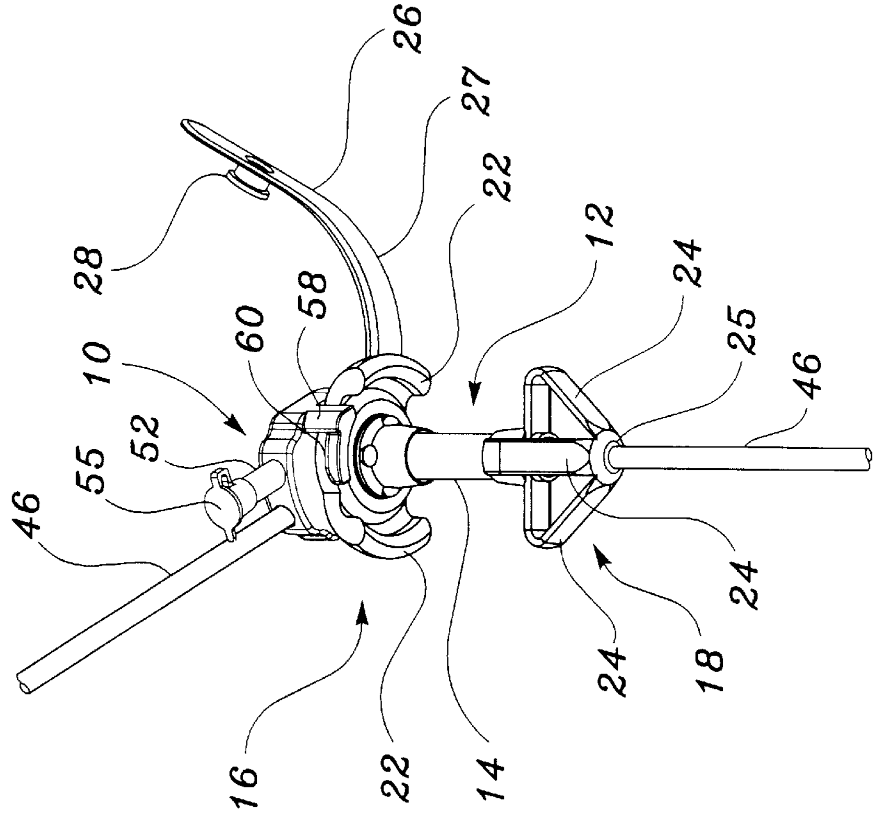
FIG. 8 is a perspective view of the preferred embodiment of the low profile jejunal adapter disposed on the low profile gastrostomy tube in an unlatched position according to the present invention.

Referring to the drawings, the preferred embodiment of the low profile jejunal adapter for a low profile gastrostomy tube of the present invention is illustrated and generally indicated as 10 in FIG. 1. The low profile jejunal adapter 10 is configured to be used with a low profile gastrostomy tube 12, as illustrated in FIG. 8. Preferably, the low profile gastrostomy tube 12 includes a hollow tubular member 14 having an external retention member 16 at one end and an internal retention member 18 at the other end with a lumen (not shown) that axially extends through gastrostomy tube 12. External retention member 16 and internal retention member 18 may be attached, bonded or integrally formed with tubular member 16.

Figure 10:
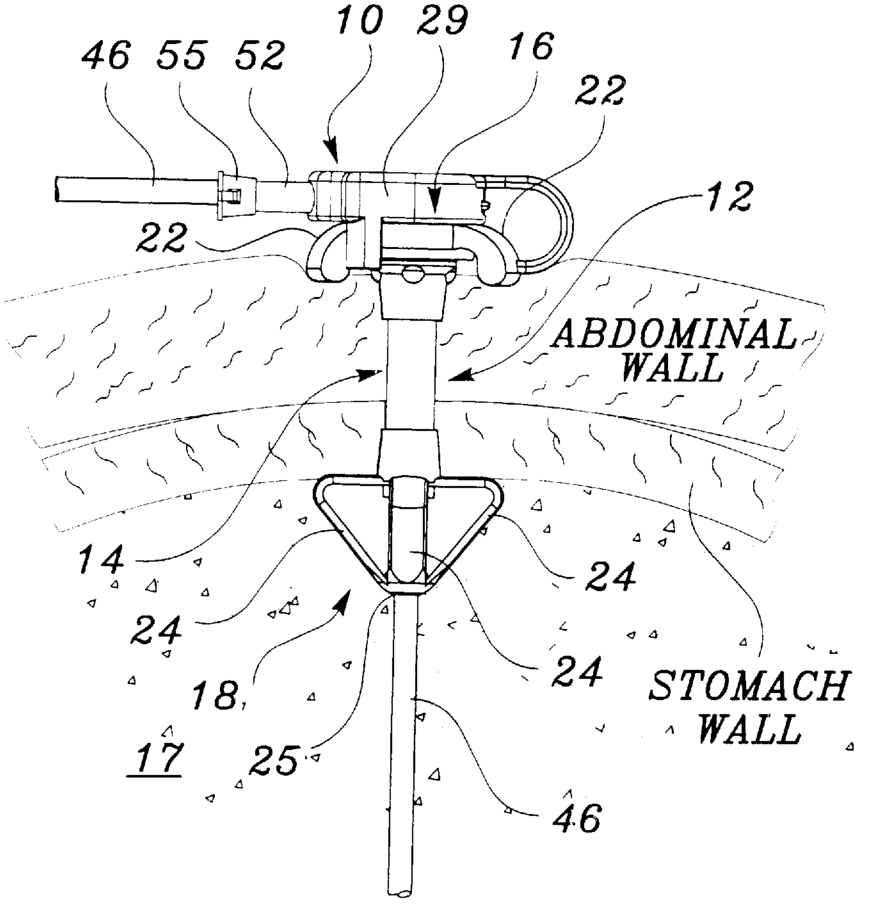
FIG. 10 is a side view of the preferred embodiment of the low profile jejunal adapter attached to the low profile gastrostomy tube in the latched position deployed within in a patient according to the present invention.

Referring to FIG. 10, the preferred embodiment of the low profile gastrostomy tube 12 will be discussed in greater detail. External retention member 16 comprises a body 29 having an axial opening (not shown) and opposed legs 22 which are adapted to abut the outer abdominal wall (FIG. 10) of a patient and securely seat retention member 16 thereon. Internal retention mechanism 18 comprises a plurality of flexible retaining arms 24 with an orifice 25 formed through the distal end thereof which are releasably expandable within a hollow visceral organ, e.g., the stomach, of a patient when inserted through an established, matured stoma formed through the abdominal and stomach walls of a patient and into the stomach. Once the retaining arms 24 enter the stomach, the internal retention member 18 may be used to securely anchor the abdominal and stomach walls between external retention member 16 and internal retention member 18 as shall be explained in greater detail below. As shown in FIG. 8, the gastrostomy tube 12 also includes a cap 26 having a shaft 27 extending from external retention member 16 with shaft 27 terminating at a plug 28 formed at the free end thereof. Shaft 27 is attached, formed with, or tethered to at least one of legs 22 of external retention member 16.

Referring to FIG. 10, the above described low profile gastrostomy tube 12 is deployed by inserting an obturator rod (not shown) through the axial opening of the external retention member 16 until the obturator rod registers with the orifice 25 formed through the distal end of flexible retaining arms 24. By pushing the obturator rod axially through the low profile gastrostomy tube 12, the distal end of the obturator rod pushes against orifice 25 which mechanically elongates retaining arms 24 and slenderizes arms 24 to a size slightly less than the inner diameter of an established matured stoma of a patient such that the tubular member 14 and internal retention member 18 may be easily inserted or removed through the stoma and the stomach. After internal retention member 18 has been inserted inside the stomach, the obturator rod is withdrawn through tubular member 14 which causes flexible retaining arms 24 of internal retention member 18 to assume their preset, enlarged shape. The user then affixes the stomach against the posterior abdominal wall by pulling the anchored internal retention member 18 towards the abdominal wall. Once the abdominal and stomach walls are securely anchored between the internal retention member 18 and the external retention member 16 the low profile gastrostomy tube 12 is connected with a tube administration set (not shown) to establish fluid flow communication between a source of fluid (not shown) and the patient's stomach.

Figure 9:
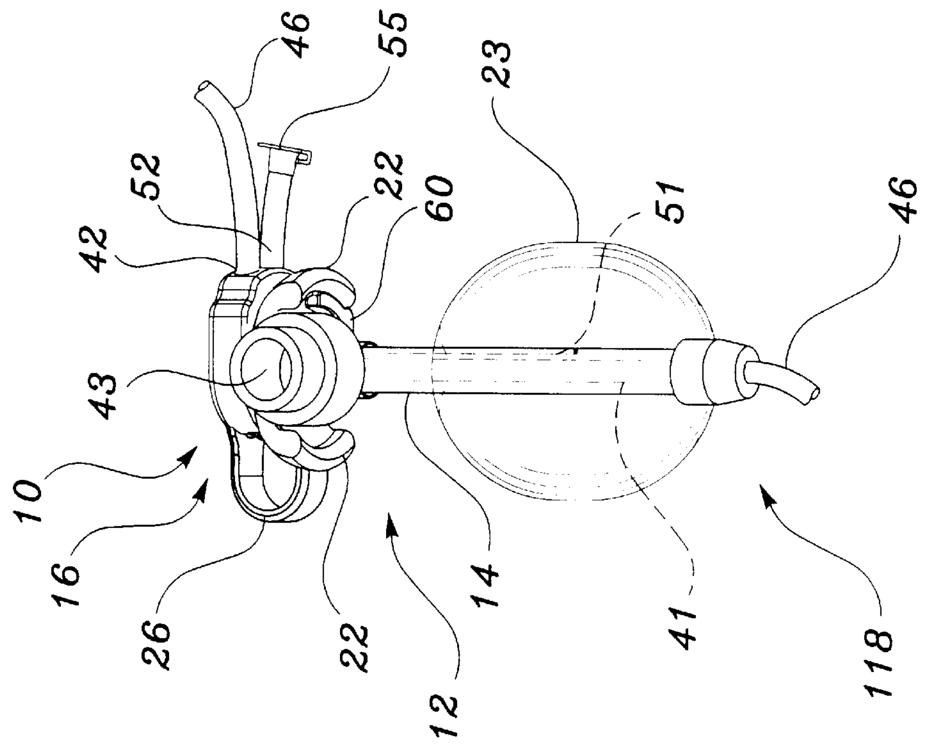
FIG. 9 is a perspective view of the preferred embodiment of the low profile jejunal adapter disposed on an alternate embodiment of the low profile gastrostomy tube having an inflatable balloon.

In an alternative embodiment of low profile gastrostomy tube 12, which may be used with the low profile jejunal adapter 10 as shown in FIG. 9, all the elements of the gastrostomy tube are the same; however, internal retention member 118 has an inflatable balloon 23 instead of flexible retaining arms 24 to anchor gastrostomy tube 12 within stomach 17. Inflatable balloon 23 further includes a primary lumen 41 which extends through tubular member 14 for directing a feeding tube 46 therethrough and a secondary lumen 51 which extends axially through tubular member 14 and communicates with a one-way valve 43 formed on body 29 for injecting fluid in order to inflate balloon 23. Similar to the preferred embodiment, the internal retention member 118 is inserted through an established, matured stoma of a patient with inflatable balloon 23 in the deflated condition until it reaches the stomach. To inflate balloon 23, the user engages a syringe (not shown) or other suitable device and injects fluid through one-way valve 43 until balloon 23 is fully inflated and securely anchored within the stomach.

Figure 2:
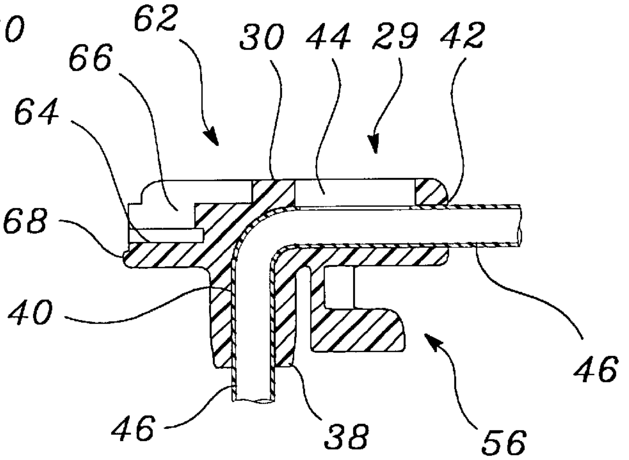
FIG. 2 is a side cross-sectional view of a preferred embodiment of the low profile jejunal adapter according to the present invention.
Figure 3:
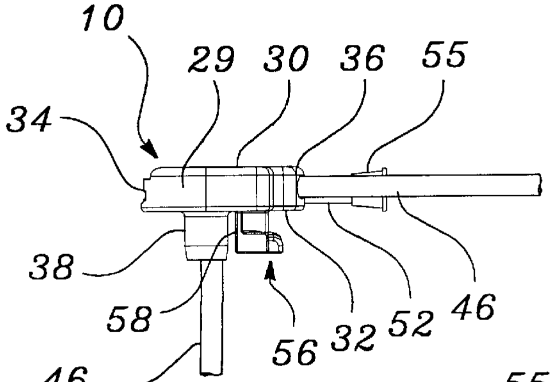
FIG. 3 is a side view of a preferred embodiment of the low profile jejunal adapter according to the present invention.
Figure 4:
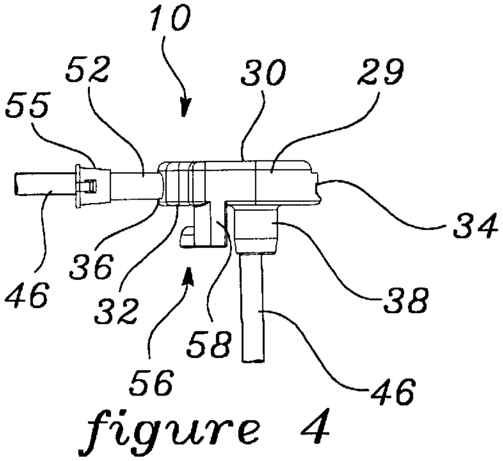
FIG. 4 is an opposite side view of a preferred embodiment of the low profile jejunal adapter shown in FIG. 3 according to the present invention.

As shown in FIGS. 1 and 3 low profile jejunal adapter 10 of the present invention includes a body 29 having opposing upper and lower surfaces 30 and 32 and opposing forward and rearward positions 34 and 36. With reference to FIG. 2, body 29 further comprises a protrusion 38 extending axially from lower surface 32 with a primary lumen 40 formed therethrough which communicates with a primary port 42 through a channel 44. Channel 44 is formed along upper surface 30 and has an arcuate shape which permits primary lumen 40 to communicate with primary port 42. As further shown, protrusion 38 is sized and shaped to be receivable within the axial opening of the external retention member 16 in order to engage the low profile jejunal adapter to the low profile gastrostomy tube 12.

Low profile jejunal adapter 10 further includes a feeding tube 46 which is sized and shaped to be inserted through the primary port 42, channel 44 and primary lumen 40 of the jejunal adapter 10 as well as tubular member 14 and orifice 25 of the low profile gastrostomy tube 12. Feeding tube 46 is constructed of a flexible elastomeric material such that tube 46 may be guided along a pathway through jejunal adapter 10, low profile gastrostomy tube 12, the stomach and the pyloric sphincter (not shown) such that the distal end of feeding tube 46 terminates within the jejunum of a patient. Feeding tube 46 includes a plurality of radial apertures (not shown) formed along the distal end thereof to ensure proper fluid outflow from feeding tube 46 and into the jejunum. Further, the distal portion of feeding tube 46 may have a coiled configuration or include a plurality of weights (not shown) to assist in maintaining the distal end of tube 46 within the jejunum.

Referring to FIG. 10, once the distal end of feeding tube 46 is properly positioned within the jejunum, the proximal end of feeding tube 46 is inserted through primary lumen 40, channel 44, and out primary port 42 so that tube 46 extends approximately parallel relative to the abdomen of the patient at a substantially low profile. Once feeding tube 46 is properly positioned within the jejunum, the proximal end of feeding tube 46 may then be cut to any desirable length and connected to a tube administration set through an adapter (not shown) which is in turn connected to the source of fluid for fluid delivery to the patient.

Figure 5:
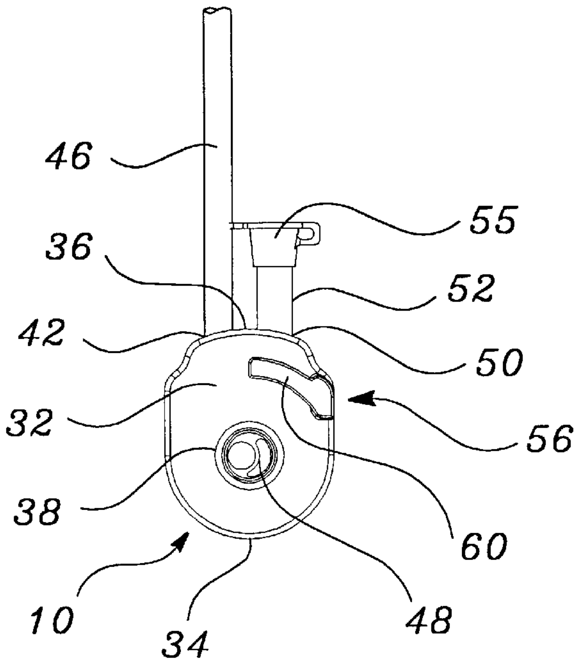
FIG. 5 is a bottom plan view of a preferred embodiment of the low profile jejunal adapter according to the present invention.
Figure 6:
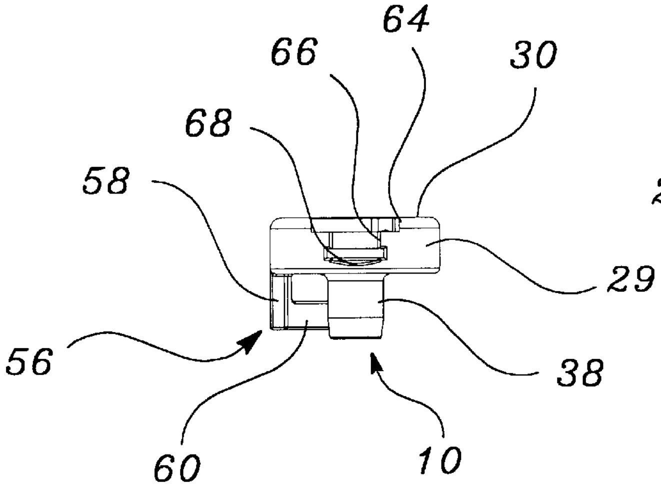
FIG. 6 is a front view of the preferred embodiment of the low profile jejunal adapter according to the present invention.
Figure 7:
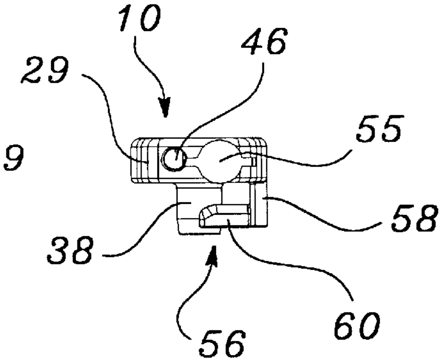
FIG. 7 is a rear view of the preferred embodiment of the low profile jejunal adapter according to the present invention.

Referring to FIG. 5, low profile jejunal adapter 10 further comprises a generally half-moon shaped venting lumen 48 extending through protrusion 38 and body 29 which permits gas to be vented from the stomach through adapter 10, while simultaneously supplying fluid directly through feeding tube 46. Venting lumen 48 communicates with a venting port 50 located at the rearward portion 36 of body 29 with a venting tubular extension 52 extending longitudinally from venting port 50. As shown in FIG. 1, a venting tubular extension 52 includes a cap 55 attached to the free end thereof for sealing venting port 50.

As illustrated in FIGS. 3, 4, 5, 6 and 7 another unique aspect of the present invention is that low profile jejunal adapter 10 includes a latching mechanism 56 for securing adapter 10 to low profile gastrostomy tube 12. Latching mechanism 56 includes a leg 58 which extends from the lower surface 32 with a finger 60 formed at a distal end thereof. As best appreciated with reference to FIG. 10, leg 58 functions to space finger 60 a distance from body 29 so that external retention member 16 can be securely engaged between lower surface 32 and finger 60. To secure low profile jejunal adapter 10 to the external retention member 16, the user securely engages finger 60 in the space formed between protrusion 38 and one of legs 22 of retention member 16.

Referring to FIGS. 1 and 8, another unique aspect of the low profile jejunal adapter 10 is that it includes a cap retention mechanism 62, for retaining the cap 26, shaft 27 and plug 28 of the low profile gastrostomy tube 12. Cap retention mechanism 62 includes a depression 64 formed in upper surface 30 for securing the cap 26, shaft 27 and plug 28 thereon. As further shown, depression 64 has a U-shaped groove 66 formed in the forward portion 34 of upper surface 30 and a U-shaped undercut 68 formed below and aligned with the U-shaped groove 66. To retain cap 26 therein, depression 64 is sized and shaped to receive the cap 26, as shown in FIG. 8, while the U-shaped groove 66 and U-shaped undercut 68 are configured to receive shaft 27 and plug 28, respectively.

In operation, as best appreciated with reference to FIGS. 2, 8, 9 and 10, the user of the present invention threads the feeding tube 46 through primary port 42, channel 44 and primary lumen 40 so that it extends outwardly from protrusion 38. Once feeding tube 46 extends outwardly from protrusion 38, the user threads the feeding tube 46 through low profile gastrostomy tube 12, which has been properly positioned within an established, matured stoma of a patient, and feeds feeding tube 46 through a patient's stomach, past the pyloric sphincter, and into the jejunum. The feeding tube 46 is directed into the jejunum by manipulating a stylet, guide wire, or suture (not shown) by the user. For example, a semi-rigid stylet may be inserted within feeding tube 46 to stiffen it and assist in directing the feeding tube 46 through the patient and into the jejunum. Alternatively, a guide wire may be run through the pyloric sphincter and into the jejunum. Once properly positioned, the feeding tube 46 is guided along the guide wire until it reaches the jejunum. The present invention may also be positioned within the jejunum by use of an endoscope (not shown) which grasps a suture wire and drags the feeding tube 46 into the jejunum.

As shown in FIG. 8, after feeding tube 46 is properly positioned within the jejunum, the user latches low profile jejunal adapter 10 to gastrostomy tube 12 by inserting protrusion 38 within the axial opening of external retention member 16. The user then rotates low profile jejunal adapter 10 relative to low profile gastrostomy tube 12 so that one of legs 22 of external retention member 16 is secured between finger 60 of the latching mechanism 56 and lower surface 32 of the jejunal adapter 10. After low profile jejunal adapter 10 is properly latched to low profile gastrostomy tube 12, the user may then cut the proximal end of the feeding tube 46 to any desirable length so that an adapter may be attached thereto for connection to the feeding set. As such, the user may utilize the present invention with a variety of patients of differing ages or builds since feeding tube 46 may be sized to accommodate the particular distance of the pathway between the low profile jejunal adapter 10 and patient's jejunum. Finally, with reference to FIGS. 2, 8 and 10, cap 26 is secured to low profile jejunal adapter 10 by inserting cap 26 within depression 64 while inserting shaft 27 and plug 28 within U-shaped groove 66 and U-shaped undercut 68, respectively.

To vent gas from the stomach while simultaneously feeding fluid to the jejunum, the user need only disengage the cap 55 of the venting tubular extension 52. With cap 55 disengaged, gas from the stomach may escape into the tubular member 14 where it enters venting lumen 48 and is evacuated out venting tubular extension 52. To stop venting, the user simply engages cap 54 back on venting tubular extension 52.

Although the above described device achieves the objects and advantages desired, an alternative embodiment of the low profile jejunal adapter 10 is also contemplated to fall within the scope of the present invention. As best appreciated with reference to FIG. 11, the alternative embodiment comprises a low profile jejunal adapter 110 includes a body 129 having opposing upper and lower surfaces 130, 132 and opposing forward and rearward portions 134 and 136. Body 129 further includes a protrusion 138 extending axially from lower surface 132 with a primary lumen 140 and a venting lumen 148 extending axially therethrough. Referring to FIG. 12, body 129 also includes a primary port 142 in communication with a hole 170 formed through upper surface 130 for receipt of a stylet, or guide wire, (not shown) to assist in directing a feeding tube 146 into the jejunum of a patient. A pair of slots 172 are also formed along upper surface 130 of body 129 for retaining a plate 74 (FIG. 14) as will be discussed in greater detail below. Protrusion 138 is engageable with the axial opening of the external retention member 16 such that feeding tube 146 may be inserted through gastrostomy tube 12.

Figure 14:
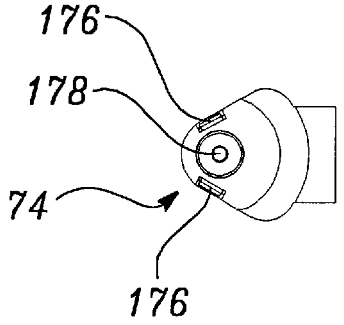
FIG. 14 is a bottom perspective view of a plate used with the alternative embodiment of the low profile jejunal adapter according to the present invention.

Referring to FIG. 14, releasably attachable to body 129 is a plate 74 sized to be fitted over and seal the upper surface 130 of low profile jejunal adapter 110. The plate 74 comprises a pair of tabs 176 engageable with the pair of slots 172 formed in the upper surface 130 to secure plate 74 to body 129 once tabs 176 are engaged therein. Plate 74 also includes a plug member 178 axially extending therefrom which is adapted to seal hole 170 from fluid flow communication when plate 74 is engaged to upper surface 130.

Figure 12:
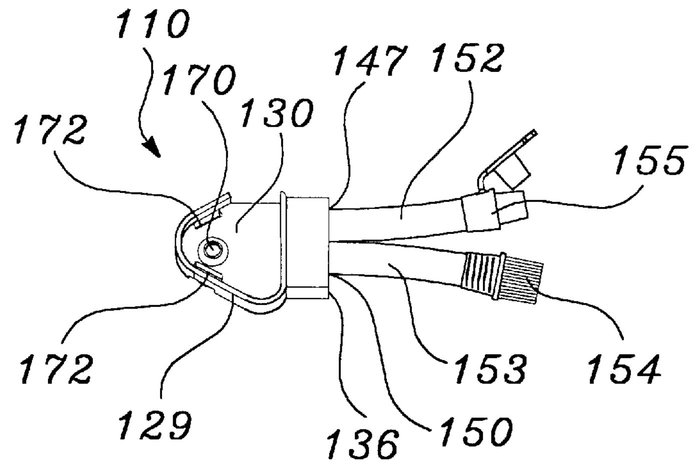
FIG. 12 is a top plan view of an alternative embodiment of the low profile jejunal adapter according to the present invention.
Figure 13:
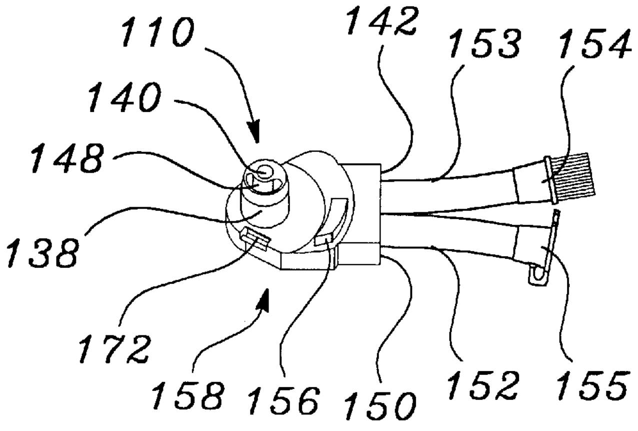
FIG. 13 is a bottom perspective view of the alternative embodiment of the low profile jejunal adapter according to the present invention.

Referring to FIG. 13, a venting lumen 148 is axially formed through the protrusion 138 and has a similarly half-moon shaped configuration as the preferred embodiment which allows for venting of gas from the stomach, while fluid is simultaneously fed to the patient's jejunum through feeding tube 146. Venting lumen 148 communicates with a venting port 142 (FIG. 12) which has a venting tubular extension 153 extending therefrom. As further shown, venting tubular extension 153 has a screw cap 154 attachable thereto for sealing tubular extension 153 to fluid flow when the user does not want to vent gas from the stomach.

Another aspect of the alternative embodiment is that low profile jejunal adapter 110 includes a latching mechanism 156 for securing adapter 110 to the low profile gastrostomy tube 12. As particularly shown in FIG. 11, latching mechanism 156 includes a leg 158 extending from body 129 with a finger 160 formed at a distal end thereof. Leg 158 functions to space finger 160 a distance from body 129 so that one of the legs 22 of external retention member 16 can be securely engaged between lower surface 132 and finger 160 of low profile jejunal adapter 110 when engaging adapter 110 to gastrostomy tube 12.

Figure 11:
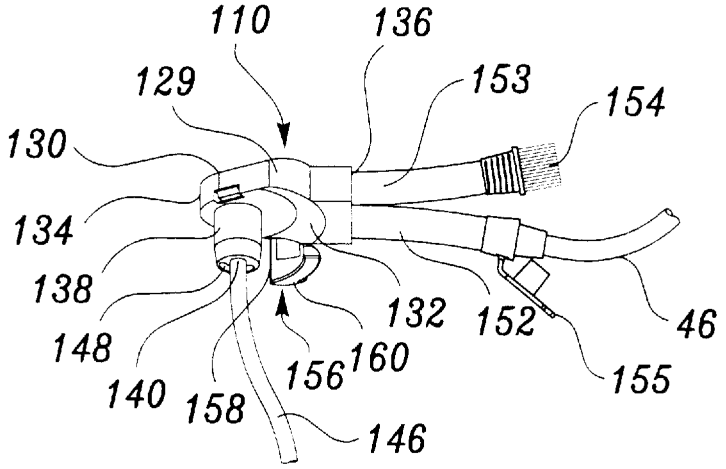
FIG. 11 is a perspective view of an alternative embodiment of the low profile jejunal adapter according to the present invention.

According to another aspect of the present invention shown in FIGS. 11, 12 and 13, low profile jejunal adapter 110 includes a tubular extension 152 having a cap 155 tethered at the free end thereof that can close off extension 152 to fluid flow when sealed thereto.

Another distinguishing feature of the alternative embodiment from the preferred embodiment is that the feeding tube 146 is fixedly attached to the primary lumen 140 and has a predetermined length. In contrast, feeding tube 146 of the preferred embodiment is threaded through body 29 after the distal end of tube 146 is positioned within the jejunum and the excess cut away. Since the distance to a patient's jejunum from the stomach may vary from patient to patient depending on age or build, jejunal adapters 110 of this type are manufactured having a feeding tube 146 with differing lengths to accommodate patients of different sizes. Low profile jejunal adapter 110 is manufactured in accordance with the alternative embodiment minimizes the manufacturing costs by reducing the amount of feeding tube 146 utilized to the precise length required.

In operation, as shown in FIGS. 12–14, the user of the above disclosed alternative embodiment will select a low profile jejunal adapter 110 having a feeding tube 146 fixedly attached to primary lumen 140 with an appropriate length for positioning the distal end of feeding tube 146 in the jejunum for a particular patient. Feeding tube 146 is then inserted through low profile gastrostomy tube 12 and into a patient's stomach. The user then directs distal end of feeding tube 146 through the pyloric sphincter and into the jejunum of the patient. Once properly positioned within the jejunum of the patient, the user will latch the jejunal adapter 110 to the low profile gastrostomy tube 12 using latching mechanism 156 and plate 74 is then secured over hole 170 with plug member 178 inserted therein for sealing hole 170. Finally, the proximal end of feeding tube 146 is pulled through the primary tubular extension 152 and attached to an adapter (not shown) which in turn is connected to a feeding set for supplying fluid from a fluid source (not shown) to the jejunum. Similar to the operation of the preferred embodiment, the user may vent gas from the patient's stomach by simply unscrewing the cap 153 from the venting tubular extension 153 which allows gas to escape through the low profile gastrostomy tube 12 and low profile jejunal adapter 110.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

We claim:

1. A gastrojejunal feeding system comprising:

an adapter, said adapter including a body having a protrusion extending from said body with a primary lumen formed through said protrusion, said body further including a channel formed through said body in communication with said primary lumen and extending through said body at a generally perpendicular angle relative to said primary lumen;

a gastrostomy tube, said gastrostomy tube having a distal end and a proximal end with a lumen formed therebetween, said distal end in communication with a visceral organ of a patient and said proximal end being attachable to said protrusion of said adapter; and a feeding tube having a distal end and a proximal end, said proximal end being insertable through said gastrostomy tube and said adapter;

wherein said feeding tube extends from said adapter at a low profile relative to a patient.

2. The gastrojejunal feeding system according to claim 1, wherein said body further includes a primary port formed adjacent said channel.

3. The gastrojejunal feeding system according to claim 2, wherein said proximal end of said feeding tube extends from said adapter at a low profile relative to a patient from said primary port.

4. The gastrojejunal feeding system according to claim 1, wherein said body further includes a venting lumen formed through said protrusion, said body further including a venting port in communication with said venting lumen.

5. The gastrojejunal feeding system according to claim 4, wherein said body further including a tubular extension in communication with said venting port.

6. The gastrojejunal feeding system according to claim 1, wherein said adapter further including a means for releasably latching said adapter to said gastrostomy tube.

7. The gastrojejunal feeding system according to claim 6, wherein said means for releasably latching comprises a leg extending from said body, said means further comprising a finger formed at a free end of said leg and extending at a generally perpendicular angle relative to said leg.

8. The gastrojejunal feeding system according to claim 1, wherein said proximal end of said gastrostomy tube comprises an external retention member and a cap formed with said external retention member and wherein said body further includes a means for securing said cap to said adapter.

9. The gastrojejunal feeding system according to claim 8, wherein said means for securing said cap comprises a U-shaped groove formed in said body, said means for securing said cap further comprising a U-shaped undercut formed in said body adjacent said U-shaped groove.

10. The gastrojejunal feeding system according to claim 1, wherein said distal end of said feeding tube terminates within a jejunum of a patient.

11. The gastrojejunal feeding system according to claim 10, wherein fluid may be supplied to a jejunum of a patient through said feeding tube.

12. The gastrojejunal feeding system according to claim 11, wherein gas contained within a visceral organ of a patient may be evacuated through said venting lumen and out said tubular extension of said adapter.

13. The gastrojejunal feeding system according to claim 12, wherein said adapter may evacuate gas from a visceral organ of a patient while supplying fluid to a jejunum of a patient.

14. The gastrojejunal feeding system according to claim 1, wherein gas contained within a visceral organ of a patient may be evacuated through said venting lumen and out said tubular extension of said adapter.

15. A gastrojejunal feeding system comprising:

an adapter, said adapter including a body having a protrusion extending from said body and a primary lumen formed through said protrusion, said body further including an open channel in communication with said primary lumen, said body further including a venting lumen formed through said protrusion;

a gastrostomy tube, said gastrostomy tube having a distal end and a proximal end with a lumen formed therebetween, said distal end being in communication with a visceral organ of a patient and said proximal end being attachable to said protrusion of said adapter, said primary lumen and said venting lumen being in communication with said lumen of said gastrostomy tube; and a feeding tube having a distal end and a proximal end, said distal end being insertable through said gastrostomy tube and said adapter, said feeding tube being adapted to transport fluid therethrough;

wherein said adapter may provide fluid to a jejunum while simultaneously evacuating gas from a visceral organ of a patient.

16. The gastrojejunal feeding system according to claim 15, wherein said body further includes a venting port in communication with said venting lumen.

17. The gastrojejunal feeding system according to claim 16, wherein said body further includes a tubular extension connected to said venting port.

18. The gastrojejunal feeding system according to claim 17, wherein gas is evacuated from said adapter through said tubular extension.

19. The gastrojejunal feeding system according to claim 15, wherein said body further includes a means for releasably latching said adapter to said gastrostomy tube.

20. The gastrojejunal feeding system according to claim 19, wherein said means for releasably latching includes a leg extending from said body, said means further including a finger formed at a free end of said leg and extending approximately perpendicular angle relative to said leg.

21. The gastrojejunal feeding system according to claim 15, wherein said gastrostomy tube includes an external retention member and a cap formed with said external retention member, wherein said body includes an upper surface defining a means for securing said cap.

22. The gastrojejunal feeding system according to claim 21, wherein said means for securing said cap comprises a U-shaped groove formed through said upper surface, said means for securing said cap further comprising a U-shaped undercut formed through said upper surface adjacent said U-shaped groove.

23. The jejunal adapter according to claim 22, wherein said body further includes a means for releasably latching said body to a low profile gastrostomy tube.

24. The jejunal adapter according to claim 23, wherein said means for releasably latching comprises a leg extending perpendicular relative to said body, said means further comprising a finger formed at a distal end of said leg and extending approximately perpendicular relative to said leg.

25. The gastrojejunal feeding system according to claim 15, wherein gas is evacuated from a visceral organ of a patient through said venting lumen.

26. A method for a feeding fluid to a jejunum while simultaneously evacuating gas from a visceral organ of a patient using a gastrojejunal feeding system comprising an adapter, the adapter including a body having a protrusion extending from the body with a primary lumen in communication with a channel formed through a body, the body further including a venting lumen with a tubular extension attached to the venting lumen and a primary port in communication with the channel, the tubular extension including a cap for sealing the tubular extension, a gastrostomy tube having a distal end and a proximal end with a lumen formed therebetween, the distal end being in communication with a visceral organ of a patient and the proximal end being attachable to the protrusion of the adapter, the primary lumen and the venting lumen being in communication with the lumen of the gastrostomy tube, a feeding tube having a distal end and a proximal end, the method comprising the steps of:

a) threading the distal end of the feeding tube through the primary lumen;

b) directing the distal end of the feeding tube through the gastrostomy tube;

c) feeding the distal end of the feeding tube through a visceral organ and into the jejunum of a patient;

d) attaching the adapter to the gastrostomy tube;

e) directing the proximal end of the feeding tube along the channel and outward through the primary port;

f) cutting off the proximal end of the feeding tube and attaching the proximal end of the feeding tube to a feeding set in communication with a source of fluid;

g) providing fluid to a jejunum of a patient through the feeding tube; and h) removing the cap from the tubular extension and permitting gas to evacuate from a visceral organ of a patient.

27. The method according to claim 26, wherein said step d) further includes the step of attaching the feeding set to a source of fluid.

28. The method according to claim 26, wherein said step e) includes directing the proximal end of the feeding tube outward through the primary port at a low profile relative to a patient.

29. The method according to claim 26, wherein said step (d) includes inserting the protrusion of the adapter into the lumen of the gastrostomy tube.

30. A jejunal adapter for use with a gastrostomy tube in communication within a visceral organ of a patient comprising:

a body including a protrusion extending from said body with a primary lumen formed through said body, said body further including a channel in communication with said primary lumen and extending through said body at a generally perpendicular angle relative to said primary lumen, said body further a venting lumen formed through said protrusion; and a feeding tube insertable through said body and the gastrostomy tube, wherein fluid may be provided to a jejunum of a patient while simultaneously evacuating gas from a visceral organ.

31. The jejunal adapter according to claim 30, wherein fluid is provided to a jejunum through said feeding tube.

32. The jejunal adapter according to claim 30, wherein gas is evacuated from a visceral organ through said venting lumen.

33. The jejunal adapter according to claim 30, wherein said body further includes a venting port and a tubular extension attached to said venting port.

34. The jejunal adapter according to claim 33, wherein gas is evacuated from said body through said tubular extension.

35. A jejunal adapter for use in providing fluid to a jejunum through a gastrostomy tube in communication with a visceral organ of a patient comprising: a body including a protrusion extending from said body with a primary lumen formed through said body, said body further including a channel in communication with said primary lumen and extending through said body at a generally perpendicular angle relative to said primary lumen, said body further a venting lumen formed through said protrusion; and an elongated feeding tube, a portion of said feeding tube being fixedly attached to said body and insertable through the gastrostomy tube, wherein fluid may be provided to a jejunum while simultaneously evacuating gas from a visceral organ.

36. The jejunal adapter according to claim 35, wherein a portion of said feeding tube is fixedly attached to said body at said primary lumen and said channel.

37. The jejunal adapter according to claim 35, wherein said feeding tube has a predetermined length.

38. A method for feeding fluid to a jejunum while simultaneously evacuating gas from a visceral organ of a patient using a gastrojejunal feeding system comprising an adapter, the adapter including a body having a protrusion extending from the body with a primary lumen in communication with a channel formed through the body, the body further including a venting lumen with a tubular extension attached to the venting lumen, the tubular extension having a cap for sealing the tubular extension a gastrostomy tube having a distal end and a proximal end with a lumen formed therebetween, the distal end being in communication with a visceral organ of a patient and the proximal end being attachable to the protrusion of the adapter, the primary lumen and the venting lumen being in communication with the lumen of the gastrostomy tube, a feeding tube having a distal end and a proximal end, a portion of the feeding tube being fixedly attached to the body of the adapter, the method comprising the steps of:

a) directing the distal end of the feeding tube through the gastrostomy tube;

b) feeding the distal end of the feeding tube through a visceral organ and into a jejunum of a patient;

c) attaching the adapter to the gastrostomy tube;

d) cutting the proximal end of the feeding tube and attaching the proximal end of the feeding tube to a feeding set in communication with a source of fluid;

e) providing fluid to a jejunum of a patient through the feeding tube; and f) removing the cap from the tubular extension and permitting gas to evacuate from a visceral organ of a patient.

* * * * *